United States Patent
Lokar

(10) Patent No.: US 8,029,276 B1
(45) Date of Patent: Oct. 4, 2011

(54) SELF-LIGATING ORTHODONTIC BRACKET

(76) Inventor: Robert Lokar, Beverly Hills, MI (US)

( * ) Notice: Subject to any disclaimer, the term of this patent is extended or adjusted under 35 U.S.C. 154(b) by 0 days.

(21) Appl. No.: 12/888,773

(22) Filed: Sep. 23, 2010

(51) Int. Cl.
*A61C 3/00* (2006.01)
(52) U.S. Cl. ......................................................... 433/10
(58) Field of Classification Search .............. 433/8–24, 433/215–229; 29/896.1, 896.11
See application file for complete search history.

(56) References Cited

U.S. PATENT DOCUMENTS

| | | | |
|---|---|---|---|
| 2,549,528 A | 4/1951 | Russell | |
| 3,087,244 A | 4/1963 | Huettner et al. | |
| 3,464,113 A | 9/1969 | Silverman et al. | |
| 3,772,787 A * | 11/1973 | Hanson | 433/14 |
| 3,946,488 A | 3/1976 | Miller et al. | |
| 4,492,573 A * | 1/1985 | Hanson | 433/11 |
| 4,496,318 A | 1/1985 | Connelly, Jr. | |
| 4,698,017 A * | 10/1987 | Hanson | 433/11 |
| 4,712,999 A * | 12/1987 | Rosenberg | 433/8 |
| 5,322,435 A * | 6/1994 | Pletcher | 433/11 |
| 6,042,373 A | 3/2000 | Hermann | |
| 6,220,857 B1 | 4/2001 | Abels | |
| 6,257,883 B1 * | 7/2001 | Voudouris | 433/11 |
| 6,357,194 B1 | 3/2002 | Jones, Jr. | |
| 6,607,383 B2 | 8/2003 | Abels et al. | |
| 6,632,088 B2 * | 10/2003 | Voudouris | 433/18 |
| 6,823,638 B2 | 11/2004 | Stanchfield | |
| 7,025,591 B1 | 4/2006 | Kesling | |
| 7,033,170 B2 | 4/2006 | Cordato | |
| 7,255,557 B2 * | 8/2007 | Forster | 433/11 |
| 7,267,545 B2 | 9/2007 | Oda | |
| 7,335,020 B2 | 2/2008 | Castner et al. | |
| 7,416,408 B2 | 8/2008 | Farzin-Nia et al. | |
| 7,419,375 B2 | 9/2008 | Farzin-Nia et al. | |
| 7,611,353 B2 | 11/2009 | Sommer | |
| 7,621,743 B2 | 11/2009 | Bathen et al. | |
| 7,695,277 B1 | 4/2010 | Stevens | |
| 7,704,072 B2 | 4/2010 | Damon | |
| 2005/0069833 A1 | 3/2005 | Chikami | |
| 2006/0008761 A1 | 1/2006 | Allred | |
| 2006/0269895 A1 * | 11/2006 | Voudouris | 433/27 |
| 2008/0032249 A1 | 2/2008 | Scommegna et al. | |
| 2008/0138757 A1 | 6/2008 | Lai et al. | |
| 2009/0136889 A1 | 5/2009 | Abels et al. | |
| 2009/0298003 A1 * | 12/2009 | Wei et al. | 433/9 |
| 2010/0062387 A1 * | 3/2010 | Hilliard | 433/11 |
| 2010/0151403 A1 | 6/2010 | Tuneberg et al. | |

OTHER PUBLICATIONS

F-1000 Self-Ligating Bracket, Leone S.p.a. Orthodontics and Implantology, Via P. a Quaracchi, 50, 50019 Sesto Florentino, Firenze, Italy, www.leone.it, 2 pages.

* cited by examiner

*Primary Examiner* — Todd E Manahan
*Assistant Examiner* — Yogesh Patel
(74) *Attorney, Agent, or Firm* — Reising Ethington P.C.

(57) ABSTRACT

According to one embodiment of the invention, a self-ligating orthodontic bracket apparatus has a body with an archwire slot, a lingual surface for mounting to a tooth and a guide track. The body and guide track form facing surfaces. A clip is engaged between the facing surfaces and is slideably movable in the guide track between an open position such that the archwire slot can receive an archwire and a closed position in which the clip can retain the archwire in the slot. The clip is dimensioned to extend the entire length and height of the slot in the bracket when in the closed position.

17 Claims, 3 Drawing Sheets

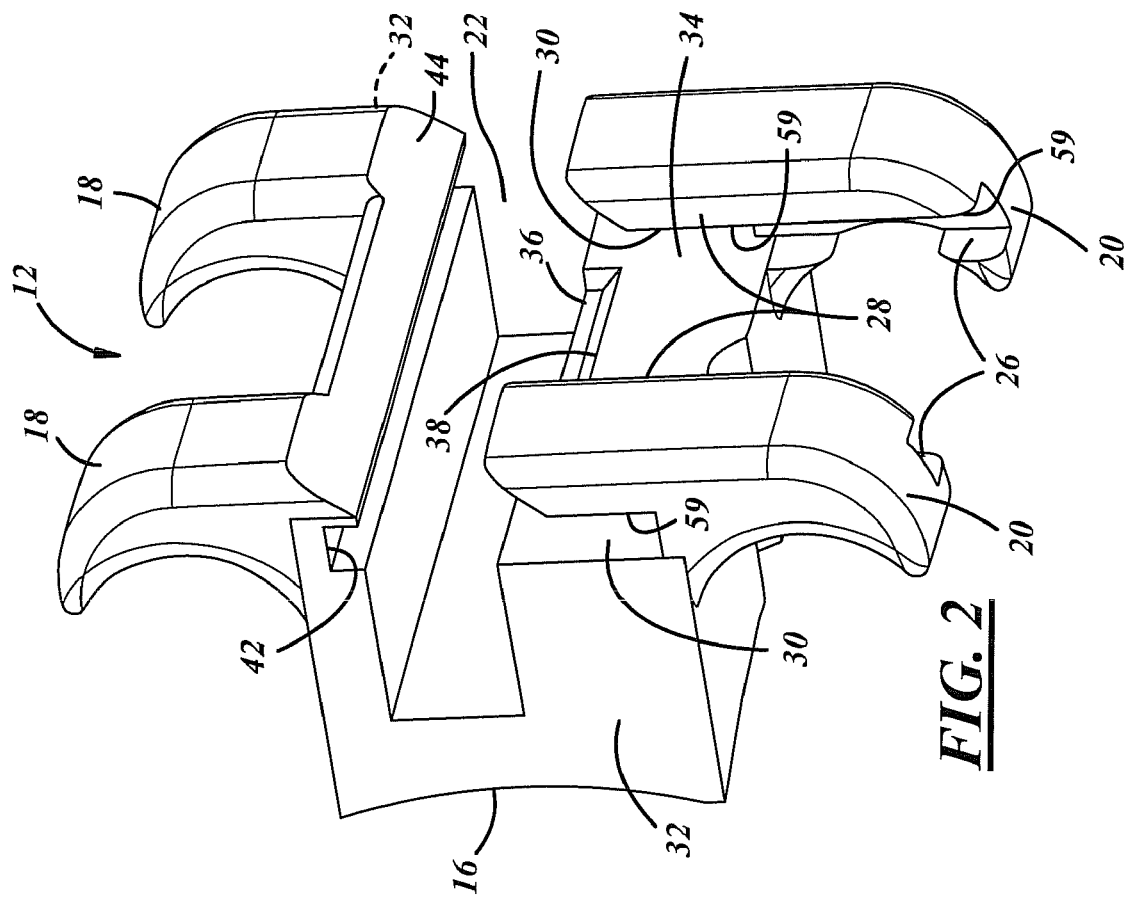
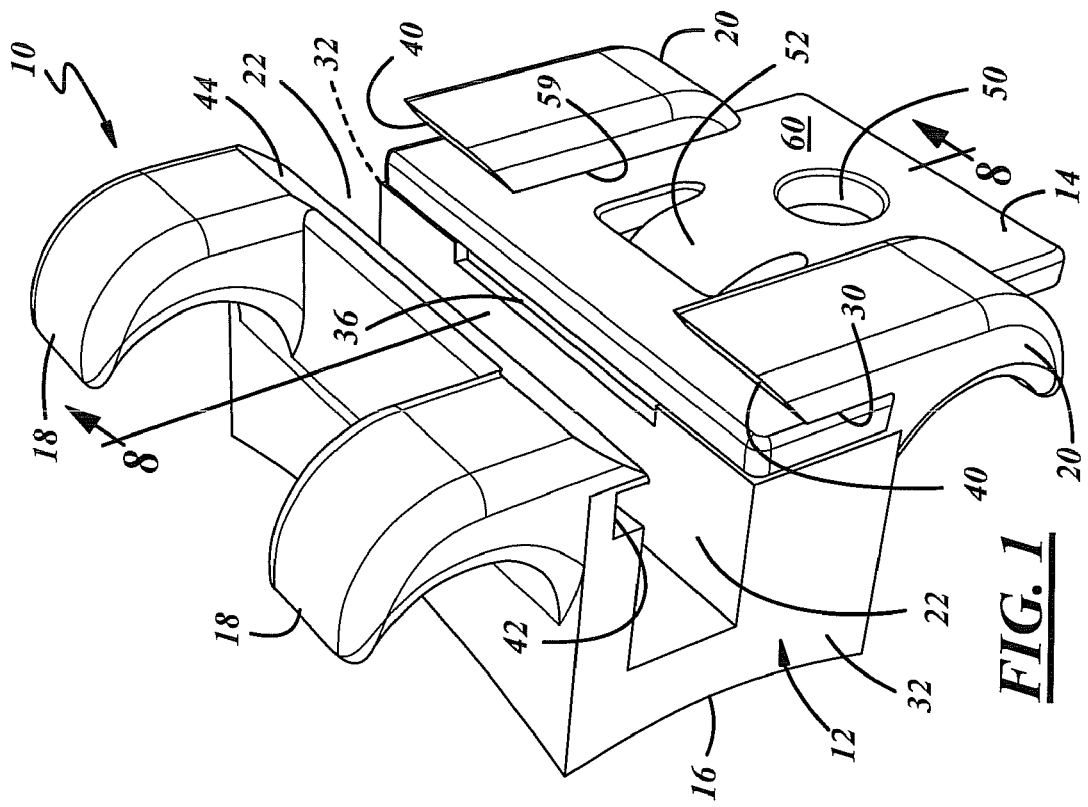

SELF-LIGATING ORTHODONTIC BRACKET

TECHNICAL FIELD

The field of this invention relates to a self-ligating orthodontic bracket.

BACKGROUND OF THE DISCLOSURE

Self-ligating orthodontic brackets are in common use for correcting irregularities of tooth position with relation to each other or in relation to the surrounding anatomy. While many different self-ligating orthodontic appliances have been devised and used, they all have drawbacks. They are either hard to install and adjust or are compromised in their ability to rotate and move teeth to the appropriate position.

What is needed is a self-ligating orthodontic bracket that is easy to install, and use and has a great capacity for rotating teeth and for performing all the functions necessary to move teeth into their proper position.

SUMMARY OF THE DISCLOSURE

According to one embodiment of the invention, a self-ligating orthodontic bracket apparatus has a body with an archwire slot, a lingual surface for mounting to a tooth and a guide track. The body and guide track form facing surfaces. A clip is engaged between the facing surfaces and is slideably movable in the guide track between an open position such that the archwire slot can receive an archwire and a closed position in which the clip can retain the archwire in the slot. The clip is dimensioned to extend the entire length and height of the slot in the bracket when in the closed position.

Preferably, a section of the clip has a tongue for movement between a first position and second position. The tongue extends into a notch in the body when in the first position and when the clip is in its closed position. The tongue abuts against the notch to retain the clip in the closed position. The facing surfaces are frictionally engaged with the clip when the tongue is in a second position and when the clip is in its open position.

Preferably, the tongue is mounted at a center section of the clip and has its first position being a normal bias position to extend into a notch in the body when the clip is in its closed position and to abut against the notch to bias and retain the clip in its closed position. The facing surfaces are frictionally engaged with the clip by resilient flexing of the tongue away from its normal bias position when the clip is in its open position.

In one embodiment, the body has cutaway outer sections extending from the guide track to the outer lateral edges of the body. The notch is located adjacent the slot and between the outer sections of the guide track. The tongue has a normal resilient bias extending lingually into the notch.

The center section has an access port that is positioned to be proximate to and extend beyond a gingival facing surface of the body when the clip is in the closed position. The gingival facing surface is accessible through the access port in the clip to allow a tool to extend through the access port and be leveraged against the gingival facing surface to exert a sliding force greater than the engagement force of the tongue in the notch. This provides flexing of the tongue outward to slide the clip from its closed position to its open position.

Preferably, the clip has a general T-shape with a crossbar section and the center section being a stem section of the T-shape. The crossbar section extends the length of the slot and the stem section contains the resilient tongue. Occlusal facing edges of the crossbar section engage the cutaway outer section of the body on both sides of the notch and the stem section engages the guide track when the clip is in the open and closed positions. An engagement slot in the body engages a gingival facing edge of the crossbar section when the clip is in the closed position.

Alternatively, the guide track may have a first and second guide track section generally facing outward toward each outer edge of the bracket. The clip may have two outer legs that engage the respective first and second guide track sections.

In accordance with another aspect of the invention, a body has a lingual surface for mounting to a tooth and an archwire slot. The body also has a guide track. The body and the guide track form facing surfaces; one of the facing surfaces has a notch therein. A clip is engaged between the facing surfaces and slideably movable in the guide track between an open position such that the archwire slot can receive an archwire and a closed position in which the clip can retain the archwire in the slot. A section of the clip has a tongue for movement between a first position and a second position often corresponding to an open position and closed position respectively of the clip. The resilient tongue extends into the notch in the body when in its first position, and when the clip is in its closed position. The tongue abuts against the notch to retain the clip in its closed position. The facing surfaces are frictionally engaged with the clip when the tongue is in its second position by resilient flexing when the clip is in its open position.

Preferably, the tongue is mounted at a center section of the clip and has its first position being a normal bias position to extend into a notch in the body when the clip is in its closed position and to abut against the notch to bias and retain the clip in its closed position. The facing surfaces are frictionally engaged with the clip by resilient flexing of the tongue away from its normal bias position when the clip is in its open position.

The center section has an access port that is positioned to be proximate to and extend beyond a gingival facing surface of the body when the clip is in the closed position. The gingival facing surface is accessible through the access port in the clip to allow a tool to extend through the access port and be leveraged against the gingival facing surface to exert a sliding force greater than the engagement force of the tongue in the notch. This provides flexing of the tongue outward to slide the clip from its closed position to its open position.

Preferably, the clip has a general T-shape with a crossbar section and center section being a stem section of the I-shape. The crossbar section extends the length of the slot and the stem section contains the resilient tongue. Occlusal facing edges of the crossbar section engage the cutaway outer section of the body on both sides of the notch. The stem section engages the guide track when the clip is in the open and closed positions. An engagement slot in the body engages a distal edge of the crossbar section when the clip is in the closed position.

In accordance with another aspect of the invention, a self-ligating orthodontic bracket apparatus has a body with an archwire slot and a lingual surface for mounting to a tooth. The body has a guide track. The body has a first beveled surface at one long side of the archwire slot beveled toward the guide track. The body has a second beveled surface at an opposing side of the archwire slot canted in the same general direction as the first beveled surface. A clip is engaged between the guide track and slideably movable between an open position such that the archwire slot can receive an archwire and a closed position in which the clip can retain the archwire in the slot. The clip is installable into the body by passing between the two beveled surfaces in front of the archwire slot to be received into the guide track.

BRIEF DESCRIPTION OF THE DRAWINGS

Reference now is made to the accompanying drawings in which:

FIG. 1 is a perspective view of one embodiment of a self-ligtating orthodontic bracket according to the invention in the open position;

FIG. 2 is a similar perspective view illustrating the base member component shown in FIG. 1;

DETAILED DESCRIPTION OF THE PREFERRED EMBODIMENT

Figure 7:
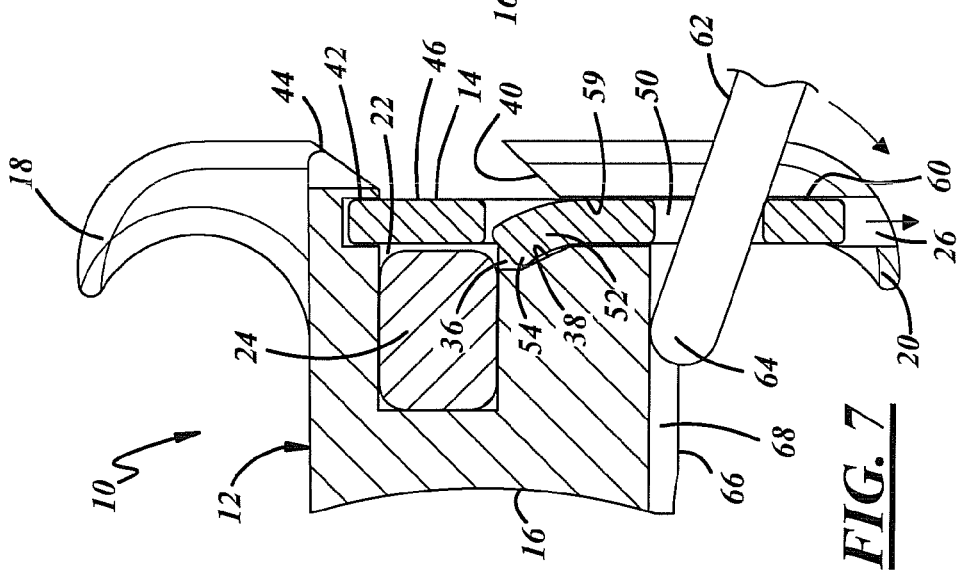
FIG. 7 is a cross-sectional view taken along lines 7-7 shown in FIG. 6 illustrating a lever tool in position to move the clip to the open position.

Referring now to FIG. 1, a self-ligating orthodontic bracket 10 has a body 12 and a clip 14. The body 12 as shown in FIG. 2 may be made from a metal material such as titanium. It has a contoured lingual surface 16 for adhering to a tooth member. The figures are oriented to show the bracket 10 as it would be basically viewed on a patient's upper teeth when the patient is sitting upright. When installed on lower teeth, the bracket 10 would be turned upside down from as shown in the drawings. A pair of gingival tie wings 18 and a pair of occlusal tie wings 20 extend from the body 12. An archwire slot 22 extends laterally through the body 12 to hold an archwire 24 as shown in FIG. 7.

Figure 6:
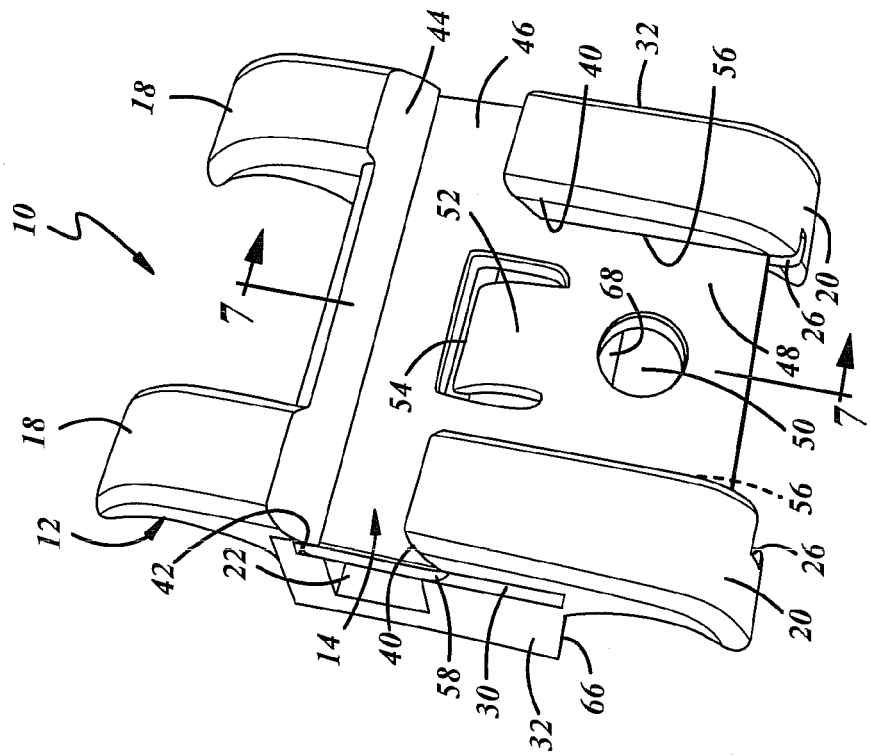
FIG. 6 is a perspective view similar to FIG. 1 showing the clip moved to the closed position.
Figure 5:
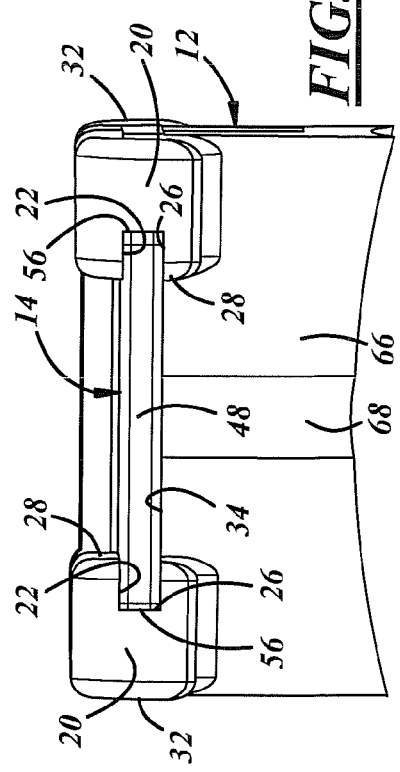
FIG. 5 is a bottom plan view of the bracket shown in FIG. 1.

As more clearly shown in FIGS. 2 and 5, two slotted internal track sections 26 i.e. track slots 26 run vertically along the axially inner edge 28 of the pair of occlusal tie wings to slideably engage the clip 14. As shown in FIGS. 1, 2 and 6, two laterally outer track sections, cutaway, or pocket sections 30 extend laterally outward from the track section 26 to the laterally outer sides 32 of the body 12. Between the occusal tie wings 20 and the track sections 26 is a labial facing surface 34 of the body member 12. A notch 36 is formed in the labial surface 34 that is adjacent the slot 22 and between the outer pocket sections 30. The notch may have a leading canted surface 38. The gingival edge of the tie wings 20 has an internal bevel 40 facing the outer pocket sections 30. An engagement slot 42 lies on the other side of slot 22 and runs the entire width between the sides 32 of the body 12 and situated under the pair of gingival tie wings 18. On the labial side of the engagement slot 42, the body 12 has a bevel edge 44 canted into slot 22. The internal bevel 40 and bevel edge 44 are canted in the same general direction.

Figure 4:
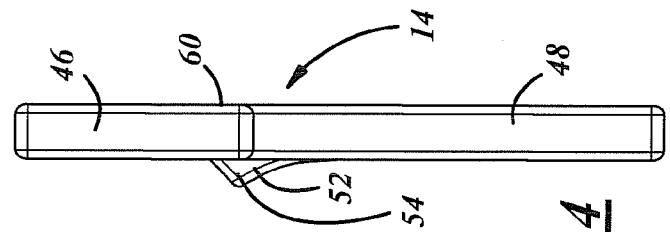
FIG. 4 is a side elevational view of the clip shown in FIG. 3.
Figure 3:
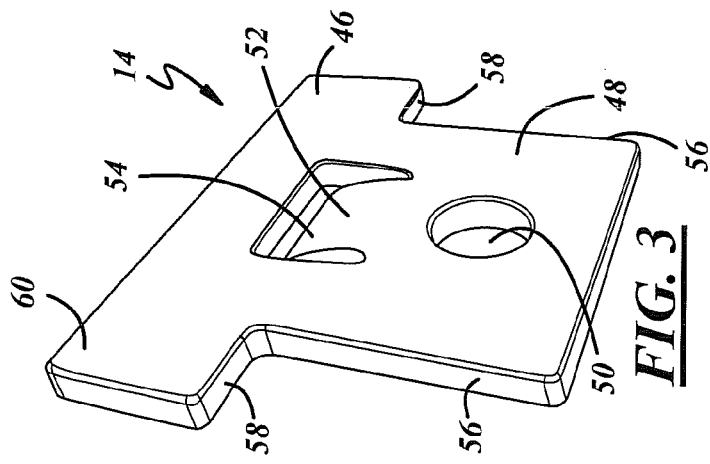
FIG. 3 is a perspective view of the clip component shown in FIG. 1.

The clip 14, as shown in more detail in FIGS. 3 and 4, has a generally T-shape with a cross bar section 46 and a stem section 48. The stem section has an access port 50 and a spring tongue member 52. As shown most clearly in FIG. 4, the distal end 54 of tongue 52 bends out of the main plane of the clip 14. Its normal position is at this bent position but the tongue can be resiliently flexed away from this normal bent position toward the main portion of the clip 14. The tongue must have a width less than the width of the notch 36 and be positioned to sit in the notch 36 as described more fully later. The clip may be made from a spring quality stainless steel or a commercially available specialized metal for example, Elgiloy™. The metal may have memory set by heat treating. The clip may have a typical thickness of about 0.007 inches. Other thicknesses between 0.003 and 0.010 inches are foreseen.

The outer edges 56 of the stem section 48 engage the track slots 26 as best shown in FIG. 5. The crossbar section as best shown in FIG. 1 engage the outer track section 30. The track slots 26 and pocket section 30 has a thickness i.e. depth slightly greater than the thickness of the clip 14 to provide sliding movement. For example, the depth may be 0.010 inches to provide a 0.003 inch clearance. Other depths and clearances are foreseen depending on the application. However, when in the open position as shown in FIG. 1 and in FIG. 8, the distal end 54 of tongue 52 resiliently engages the labial surface 34 of body 12 and the labial surface 60 of the clip 14 abuts against a lingual facing surface 59 of tie wings 20 to provide a friction to gently retain the clip 14 in position against free unintentional sliding but provide sliding motion when desired.

Figure 8:
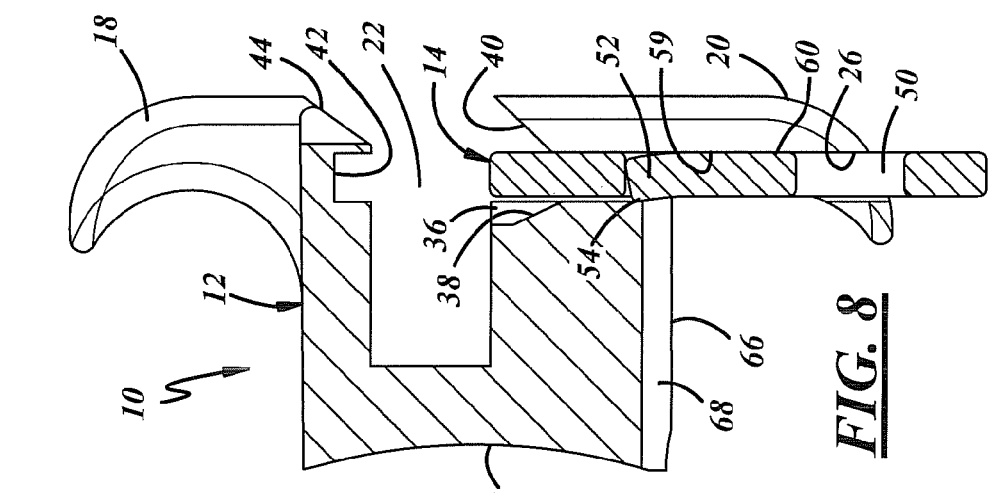
FIG. 8 is a cross-sectional view taken along lines 8-8 shown in FIG. 1.

The archwire 24, as shown in FIG. 7, is free to enter the open slot 22 when the clip is in the open position as shown in FIGS. 1 and 8. The clip 14 can then be moved by merely pushing the stem 14 to overcome the stopping friction caused by the tongue 52. The clip 14 then can be moved to the closed position as shown in FIGS. 6 and 7 thereby trapping the archwire 24 as shown in FIG. 7. The cross bar section 46 is moved up to cover the entire width of the slot 22 and the gingival edge engages the engagement slot 42. The occlusal edges 58 of the cross bar section 46 maintain engagement in the outer pocket sections 30. The outer edges 56 of stem section 48 still engage the track slots 26. The distal end 54 of the tongue 52 is allowed to resiliently bias toward its normal position into notch 36 and engage the canted surface 38. The tongue 52 thus provides a spring locking force when the clip 14 is in the closed position to prevent the clip 14 from unintentionally and undesirably slipping to the open position.

When the bracket 10 needs to be open, the access port 50 in clip 14 receives a lever tool 62 as shown in FIG. 7. The tip 64 of the lever tool engages the occlusal surface 66 of the body 12 and more particular a groove 68 shaped to align with the access port 50 when the clip 14 is in the closed position in body 12. The lever 62 is merely pivoted downwardly with the tip 64 secured against the groove 68 and abutting against port 50 in the clip 14 to overcome the locking force of the tongue 52 in the notch 36. The tongue 52 then flexes back toward the main plain of the clip and the clip 14 is then allowed to slide to the open position as shown in FIGS. 1 and 8.

The clip 14 is initially installed in the body by sliding the clip 14 against the bevel edge 44 and the clip 14 then enters the outer track section 30 via the bevel edges 40 on the other side of the slot 22. The clip 12 material has enough flexure to slip into the track slot 26 and pocket section 30 while the top bar section 46 slips into slot 22 under bevel edge 44. The clip may be installed before being heat-treated. Both the bracket body and the clip may be heat-treated at the same time.

Figure 9:
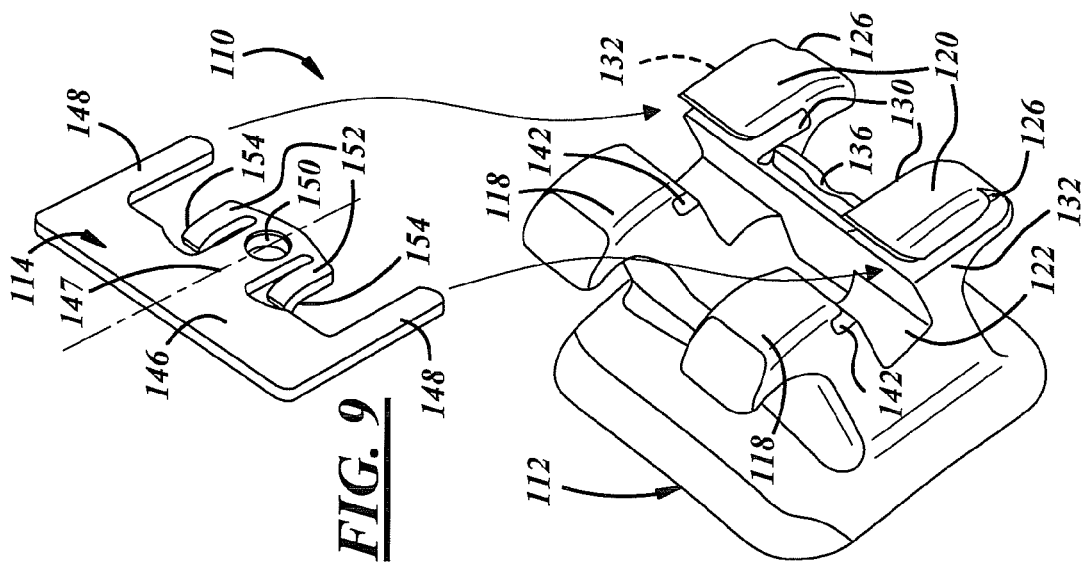
FIG. 9 is a perspective and exploded view of an alternative embodiment in accordance with the invention.

Referring now to FIG. 9, an alternate embodiment of a bracket 110 is shown where the body 112 has its occlusal tie wings 120 having track slots 126 on the lateral outer edges 132. The cutaway section or pocket section 130 adjacent the slot 122 extends laterally from the guide track toward the inner edges of the wings 120. Two engagement slots 142 extend laterally across each gingival tie wing 118 and has a gap in the middle. The clip 114 has a span section 146 and has two laterally outer legs 148 which engage the respective track slots 126 at the respective lateral outer edge 132 of the body 112. The clip 114 has a center post section 147 with the access port 150 and two resilient tongue legs 152 each with a distal end 154. The tongue ends 154 engage the ramp and notch section 136 between the track section 130 Functionally, the clip 114 and body 112 work in substantially the same fashion as the first embodiment.

In this fashion, the clip and body as described has several advantages. Firstly, it is easy to operate and does not require special tooling. It only requires a prong lever device that is a standard tool for orthodontists. The sliding motion between the open and closed positions is easy and requires no pivoting or flipping of clips or gates. Furthermore, the clip is secured in both the open and closed position against undesirable and unintentional movement. The effectiveness of the bracket is greater than standard brackets because the entire width of the bracket can be used to help create de-rotation of the teeth. Greater rotational forces can be created against the archwire in the desired direction to provide better de-rotation effects on the tooth when a larger lateral surface is used against the archwire.

Variations and modifications are possible without departing from the scope and spirit of the present invention as defined by the appended claims.

The embodiments in which an exclusive property or privilege is claimed are defined as follows:

1. A self-ligating orthodontic bracket apparatus comprising:
   a body having a slot for an archwire and a lingual surface for mounting to a tooth;
   said body having a guide track;
   said body and said guide track forming facing surfaces;
   a clip engaged between said facing surfaces and slideably movable in said guide track between an open position such that said archwire slot can receive an archwire and a closed position in which said clip can retain the archwire in said slot with said clip being supported by one of said facing surfaces of said guide track and opposite lateral edges of said body against labial directed forces exerted by said archwire;
   said clip being extending the entire length and height of said slot in said bracket when in the closed position; and
   said body having a cutaway section being in the form of a pocket section connected to and extending laterally from said guide track to receive a laterally extending portion of said clip when in said open position.

2. A self-ligating orthodontic bracket apparatus as defined in claim 1 further comprising:
   a section of said clip having a tongue for movement between a first position and second position;
   said tongue extends into a notch in said body when in said first position and when said clip is in its closed position to abut against the notch to retain the clip in the closed position; and
   said facing surfaces being frictionally engaged with said clip when said tongue is in a second position and when said clip is in said open position.

3. A self-ligating orthodontic bracket apparatus as defined in claim 2 further comprising:
   said tongue mounted at a center section of said clip and having its first position being a normal bias position to extend into a notch in said body when said clip is in said closed position and to abut against the notch to bias and retain the clip in the closed position; and
   said facing surfaces being frictionally engaged with said clip by resilient flexing of said tongue to said second position away from its normal bias position when said clip is in said open position.

4. A self-ligating orthodontic bracket apparatus as defined in claim 3 further comprising:
   said pocket section extending to said respective opposite outer lateral edges of said body to receive distal ends of said clip that extends the entire length of said slot;
   said notch being adjacent said slot and between respective pocket sections; and
   said tongue having a normal resilient bias extending lingually into said notch.

5. A self-ligating orthodontic bracket apparatus as defined in claim 4 further comprising:
   said center section having an access port that is positioned to be proximate to and extend beyond a gingival facing surface of said body when said clip is in the closed position and being accessible through said access port in said clip to allow a tool to extend through said access port and be leveraged against said gingival facing surface to exert a sliding force greater than the engagement force of said tongue in said notch to flex said tongue outward and slide said clip from the closed position to the open position.

6. A self-ligating orthodontic bracket apparatus as defined in claim 4 further comprising:
   said clip having a general T-shape with a crossbar section and the center section being a stein section of the T-shape with the crossbar section extending the length of the slot and the stem section containing said resilient tongue;
   occlusal facing edges of said crossbar section engage the outer pocket sections of said body on both sides of said notch and the stem section engages the guide track when the clip is in the open and closed positions; and
   an engagement slot in said body engages a gingival facing edge of said crossbar section when the clip is in the closed position.

7. A self-ligating orthodontic bracket apparatus as defined in claim 5 further comprising:
   said guide track having a first and second guide track section generally facing outward toward each outer edge of said bracket; and
   said clip having two outer legs that engage the respective first and second guide track sections.

8. A self-ligating orthodontic bracket apparatus as defined in claim 1 further comprising:
   said body having a first beveled surface at one long side of said archwire slot beveled toward said guide track with an engagement slot positioned directly below said first bevel;
   said body having a second beveled surface at an opposing side of said slot canted in the same direction as the first beveled surface; and
   said clip being installable into said body by passing between said two beveled surfaces in front of said slot to be received into said guide track.

9. A self-ligating orthodontic bracket apparatus comprising:
   a body having a lingual surface for mounting to a tooth and a slot for an archwire;
   said body having a guide track;
   said body and said guide track forming facing surfaces and having a notch therein;

a clip engaged between said facing surfaces and slideably movable in said guide track between an open position such that said slot can receive the archwire and a closed position in which said clip can retain the archwire in said slot with said clip being supported by one of said facing surfaces of said guide track against labial directed forces exerted by said archwire;

a section of said clip having a tongue for movement between a first position and a second position relative to said clip;

said tongue extending into the notch in said body when in its first position and when said clip is in its closed position to abut against the notch to retain the clip in the closed position;

said facing surfaces being frictionally engaged with said clip when said tongue is in said second position by flexing when said clip is in said open position; and said body having a cutaway section being in the form of a pocket section connected to and extending laterally from said guide track to receive a laterally extending section of said clip with said clip being supported at laterally outer edges of said body against labial directed forces exerted by said archwire.

10. A self-ligating orthodontic bracket apparatus as defined in claim 9 further comprising:
said tongue mounted at a center section of said clip and having its first position being a normal bias position to extend into a notch in said body when said clip is in said closed position and to abut against the notch to bias and retain the clip in the closed position; and
said facing surfaces being frictionally engaged with said clip by resilient flexing of said tongue to said second position away from its normal bias position when said clip is in said open position.

11. A self-ligating orthodontic bracket apparatus as defined in claim 9 further comprising:
said pocket sections section extending laterally from said guide track to the outer lateral edges of said body to receive distal ends of said clip that extend the entire length of said slot;
said notch being adjacent said slot and between a respective pocket section on each side of said notch of said body; and
said tongue having a normal bias extending lingually into said notch.

12. A self-ligating orthodontic bracket apparatus as defined in claim 9 further comprising:
said section of said clip with said tongue having an access port that is positioned to be proximate to and extend beyond a gingival facing surface of said body when said clip is in the closed position and being accessible through said access port in said clip to allow a tool to extend through said access port and be leveraged against said gingival facing surface to exert a sliding force greater than the engagement force of said tongue in said notch to flex said tongue outward and slide said clip from the closed position to the open position.

13. A self-ligating orthodontic bracket apparatus as defined in claim 11 further comprising:
said clip having a general T-shape with a crossbar section and stem section with the crossbar section extending the length of the slot and the stem section containing said tongue;
occlusal facing edges of said crossbar section engage a respective pocket section of said body on both sides of said notch and the stem section engages the guide track when the clip is in the open and closed positions; and
an engagement slot in said body engages a distal edge of said crossbar section when the clip is in the closed position.

14. A self-ligating orthodontic bracket apparatus as defined in claim 9 further comprising:
said body having a first beveled surface at one long side of said slot beveled toward said guide track with an engagement slot positioned directly below said first bevel;
said body having a second beveled surface at an opposing side of said slot substantially parallel to the first beveled surface; and
said clip being installable into said body by passing between said two beveled surfaces in front of said slot to be received into said guide track.

15. A self-ligating orthodontic bracket apparatus comprising:
a body having a slot for an archwire and a lingual surface for mounting to a tooth;
said body having a guide track;
said body having a first beveled surface at one long side of said slot beveled toward said guide track;
an engagement slot positioned at an opposite side of said slot that extends the entire length of said slot;
said body having a second beveled surface at an opposing side of said slot substantially parallel to the first beveled surface and on a labial side of said of said engagement slot;
a clip engaged in the guide track and slideably movable between an open position such that said slot can receive the archwire and a closed position in which said clip can retain the archwire in said slot with the clip also extending into said engagement slot; and
said clip being installable into said body by passing between said two beveled surfaces in front of said slot to be received into said guide track; and
said body having a cutaway section being in the form of a pocket section connected to and extending laterally from said guide track to receive a laterally extending section of said clip with said clip being supported at laterally outer edges of said body against labial directed forces exerted by said archwire.

16. A self-ligating orthodontic bracket apparatus as defined in claim 15 further comprising:
said clip having a general T-shape with a crossbar section and stem section with the crossbar section extending along the length of the slot and the stem section containing a resilient tongue;
occlusal facing edges of said crossbar section engage a respective pocket section of said body on both lateral sides of a central notch and the stem section engages the guide track on both sides of said notch when the clip is in the open and closed positions; and
an engagement slot behind the second beveled surface in said body engages a distal edge of said crossbar section when the clip is in the closed position.

17. A self-ligating orthodontic bracket apparatus as defined in claim 16 further comprising:
said stem section having an access port that is positioned to be proximate to and extend beyond a gingival facing surface of said body when said clip is in the closed position and being accessible through said access port in said clip to allow a tool to extend through said access port and be leveraged against said gingival facing surface to exert a sliding force greater than the engagement force of said tongue in said central notch to flex said tongue outward and slide said clip from the closed position to the open position.

* * * * *

UNITED STATES PATENT AND TRADEMARK OFFICE
CERTIFICATE OF CORRECTION

PATENT NO.       : 8,029,276 B1                                           Page 1 of 1
APPLICATION NO.  : 12/888773
DATED            : October 4, 2011
INVENTOR(S)      : Robert Lokar It is certified that error appears in the above-identified patent and that said Letters Patent is hereby corrected as shown below:

IN THE SPECIFICATION:

| | |
|---|---|
| Column 2, line 2 | After "and the", delete "stein", insert --stem-- |
| Column 2, line 48 | After "of the", delete "I-shape", insert --T-shape-- |

IN THE CLAIMS:

| | |
|---|---|
| Claim 6, column 6, line 32 | After "being a", delete "stein", insert --stem-- |
| Claim 11, column 7, line 36 | After "sections", delete "section" |
| Claim 15, column 8, line 25 | After "of said", delete "of said" |
| Claim 15, column 8, line 30 | After "slot;", delete "and" |

Signed and Sealed this
Twentieth Day of December, 2011

David J. Kappos
*Director of the United States Patent and Trademark Office*